United States Patent [19]
Snow et al.

[11] Patent Number: 5,857,459
[45] Date of Patent: Jan. 12, 1999

[54] BOXLESS MEASUREMENT OF THORACIC GAS VOLUME

[75] Inventors: Michael G. Snow, Stacy; Steven D. James, Edina, both of Minn.

[73] Assignee: Medical Graphics Corporation, St. Paul, Minn.

[21] Appl. No.: 800,655

[22] Filed: Feb. 4, 1997

[51] Int. Cl.[6] .................................................. A61M 16/00
[52] U.S. Cl. .............................. 128/204.21; 128/204.23; 600/536; 600/538
[58] Field of Search .................................. 600/534–536, 600/538; 128/204.21, 204.23, 206.29

[56] References Cited

U.S. PATENT DOCUMENTS

| | | | |
|---|---|---|---|
| 4,258,718 | 3/1981 | Goldman | 600/538 |
| 4,267,845 | 5/1981 | Robertson, Jr. et al. | 600/538 |
| 4,269,195 | 5/1981 | Itoh | 600/538 |
| 4,373,534 | 2/1983 | Watson | 600/534 |
| 4,509,551 | 4/1985 | Luper | 600/538 |
| 4,807,640 | 2/1989 | Watson et al. | 128/721 |
| 4,817,625 | 4/1989 | Miles | 600/538 |
| 4,960,118 | 10/1990 | Pennock | 600/534 |
| 5,038,773 | 8/1991 | Norlien et al. | 128/205.23 |
| 5,099,855 | 3/1992 | Yount | 600/534 |
| 5,191,893 | 3/1993 | Reiten | 600/534 |
| 5,271,389 | 12/1993 | Isaza et al. | 128/204.21 |
| 5,318,038 | 6/1994 | Jackson et al. | 128/720 |
| 5,331,968 | 7/1994 | Williams et al. | 128/721 |
| 5,357,972 | 10/1994 | Norlien | 128/725 |
| 5,445,145 | 8/1995 | Redmon | 128/207.16 |
| 5,502,660 | 3/1996 | Anderson et al. | 364/571.03 |
| 5,513,648 | 5/1996 | Jackson | 128/721 |

OTHER PUBLICATIONS

Respitrace Ambulatory Interface Model 10.4200 User Instructions, Ambulatory Monitoring, Inc., Dec. 1987, Rev. Sep. 1991.

Snow, Michael G., "Assessment of Lung Volumes", Foundation of Respiratory Care, Chap. 45, pp. 449–455.

*Primary Examiner*—Aaron J. Lewis
*Attorney, Agent, or Firm*—Haugen and Nikolai, P.A.

[57] ABSTRACT

A portable apparatus for measuring the thoracic lung volume of a patient without enclosing the patient in a sealed chamber, comprising first and second impedance belts, a flow meter, shutter and a microprocessor-based controller. The flow meter includes pressure transducers for measuring the change in volume and pressure as the patient respires therethrough. The change in thoracic cage volume of the patient's lungs is directly correlated with the change of impedance in the belts. The thoracic lung volume is then determined from a measured barometric pressure, the measured change in pressure and the measured volume change in the thoracic cage volume utilizing a correction factor to determine the thoracic cage volume.

17 Claims, 3 Drawing Sheets

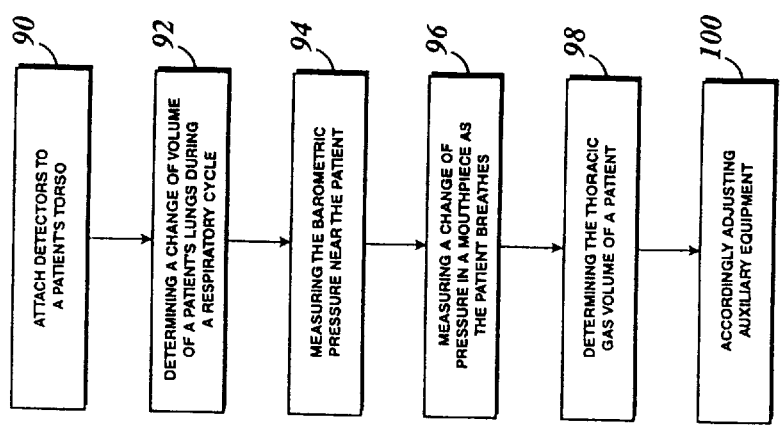

BOXLESS MEASUREMENT OF THORACIC GAS VOLUME

BACKGROUND OF THE INVENTION

I. Field of the Invention

This invention relates generally to a device used in pulmonary function testing and more particularly to a device for determining the lung volume of a patient. The device is portable and determines the thoracic gas volume of a patient without enclosing the patient in a sealed chamber. The device further includes a dynamic calibration of the device which is incorporated into the determination of the thoracic gas volume of the patient.

II. Discussion of the Related Art

The lung volume of a patient determines the anatomic and physiologic limits of the patient. These limits may be significant in the prognosis and prescribed treatment of the patient. Over the years, various methods have been used to determine the lung volume and related lung capacity of a patient. These methods have included gas dilution techniques, body plethysmography and radiographic techniques.

The gas dilution techniques include closed-circuit helium dilution, and open-circuit nitrogen washout, either by single or multiple breath techniques. A primary disadvantage of the gas dilution techniques is the inability to measure the lung volume in poorly ventilated airspaces without prolonged rebreathing. Also, gas dilution techniques require maintenance of a leak free connection to the patient, particularly during mechanical ventilatory support. Other disadvantages include difficulty in differentiating leaks in the equipment from mal-distribution, and difficulties related to adequate cleaning of the system.

Past efforts to measure a patient's lung volume using body plethysmography have required that the patient's entire body be enclosed within a sealed chamber. The cabinet interior temperature must be approximately equal to the patient's body temperature before accurate testing may commence. Often times the patient experiences discomfort, anxiety, and a feeling of being trapped within the cabinet. There are other times where a patient is not ambulatory and cannot sit within the sealed cabinet, making the use thereof difficult, if not impossible. Recognizing the need to reduce patient discomfort when using body plethysmography techniques, Andrew C. Jackson, in U.S. Pat. No. 5,513,648, discloses a partial body plethysmograph, wherein the patient's head and feet extend out from a sealed enclosure. Even in this system, the patient may experience discomfort, anxiety, and a feeling of being trapped. Thus, there still remains a need for a system and apparatus wherein the lung volume of a patient may be measured without enclosing any portion of the patient in a sealed chamber.

The radiographic techniques mentioned above also have their own shortcomings. Radiographic techniques require radiographs of the patient's lungs to be taken and analyzed, thereby exposing the patient to radiation (either x-ray or nuclear) that may be objectionable to the patient. This technique requires that the patient inspire fully and then hold the inspired breath during exposure. Additionally, oftentimes radiographic instruments are not transportable or immediately available and further, the time required to calculate the lung volume from the radiographs may preclude such use.

Therefore, a need exists for a nonintrusive device that: measures a patient's lung volume, is not affected by the surrounding airspace, does not require an ambulatory patient, and does not require a long time for measurements and calculations.

SUMMARY OF THE INVENTION

The purpose of the present invention is to provide a nonintrusive, nonradioactive, nonconfining, portable apparatus for measuring the lung volume of a patient. The apparatus of the present invention includes a microprocessor-based controller, detection means for detecting a volume change in the thoracic cage of the patient, a flow meter for determining volume change and/or pressure change measured at the mouth of the patient, and a shutter attached to the flow meter.

The flow meter of the present invention may be a pneumotachograph of the type disclosed by Norlein et al. in U.S. Pat. No. 5,038,773, which is assigned to the same assignee as the present invention, the entire disclosure of which is incorporated herein by reference. Alternatively, the flow meter described in Norlein U.S. Pat. No. 5,357,972, which is assigned to applicants' assignee, may be used, however a flow meter of the type disclosed in the '773 patent is preferred.

It is recognized that several means of detection for detecting changes in a patient's lung volume exist without requiring a sealed chamber. The present invention represents a variety of improvements in the apparatus and method of boxless measurement of thoracic gas volume which can take the form in any of several embodiments. The detailed embodiments described below are taken as representative or exemplary of those in which the improvements of the invention may be incorporated and are not presented as being limiting in any manner. In the preferred embodiment, the detection means comprises a first torso belt for detecting minute changes in the electrical impedance of a conductor surrounding the rib cage of the patient, and a second torso belt for detecting minute changes in the electrical impedance of a second conductor which surrounds the abdomen of the patient. First and second signals associated with impedance changes in the respective first and second conductors are transmitted to the controller. Without any limitation intended, the first and second belts may be of the type disclosed in U.S. Pat. No. 5,331,968, the entire disclosure of which is incorporated herein by reference. Alternatively, a plurality of electrodes may be coupled to the controller and used to determine the change in impedance between the electrodes as a measure of the volume change in a patient's lung volume as the patient inhales and exhales. Those skilled in the art will appreciate the difficulty with these devices to minimize errors in the measurement of volume change due to patient movement, change in positioning of the belts, and noise. When using impedance belts or electrodes to measure the lung volume change, there is also a recognized difficulty in maintaining the quantified relationship between volume changes and impedance changes over time due to the minimal signal to noise ratio. The present invention provides a means of calibrating the device to minimize the affects of these difficulties.

The microprocessor-based controller is electrically coupled to the detection means, the flow meter, and the shutter. Within the controller is a power supply, a means for analyzing signals generated by the detection means, the flow meter and the shutter, and a means for controlling an activation signal for activating the shutter. Signals generated by the detection means, flow meter, and shutter are analyzed to determine amounts corresponding to the change in lung volume, change in pressure, and change in flow as the patient inhales and exhales. In the preferred embodiment, the microprocessor-based controller includes software that determines the lung volume of the patient from the determined amounts of the analyzed signals.

The noninvasive apparatus is used to measure the thoracic gas volume of a patient's lungs. Prior to the measurement of the thoracic gas volume, the apparatus is calibrated. Without any limitation intended, the calibration may occur immediately before or after the thoracic gas volume of the patient's lungs is measured. In order to calibrate the apparatus the flow meter is used to determine a volume change measured at the mouth. At the same time the volume change is measured at the mouth, the change in thoracic cage volume is measured from the detection means. These measured changes are then compared to derive a correlation variable that is used to calibrate or quantify the measured thoracic cage volume changes. This correlation variable may be determined before each measurement of the thoracic gas volume.

When measuring the thoracic gas volume, the detection means attaches to a torso of the patient, and detects a change in the volume of the thoracic cage of the patient and transmits a signal corresponding to the volume change. From the transmitted signal, a microprocessor-based controller of commonly known construction assigns a value corresponding to the volume change during each respiratory cycle. At the same time this thoracic cage volume change is being measured, the patient inspires and expires against the shutter, which allows the airway pressure associated with the volume change to be measured by the differential pressure transducer. During each respiratory cycle, the change of pressure within the mouthpiece of the flow meter is measured and a corresponding signal is sent to the microprocessor-based controller. The controller then determines the thoracic gas volume from the change in thoracic cage volume measurement and the change in mouth pressure due to inhalation and exhalation, adjusting the determined thoracic gas volume according to the derived correlation variable. Once the lung volume is known, the prognosis, prescribed treatment and adjustment to auxiliary equipment may be made according to the determined thoracic gas volume.

OBJECTS

It is accordingly a principal object of the present invention to provide a nonintrusive device and method for measuring the lung volume of a patient.

Another object of the present invention is to provide a device that measures the lung volume of a patient independent of a sealed chamber or ventilated airspace surrounding at least a portion of the patient's body.

Still another object of the present invention is to provide an inexpensive device for measuring the lung volume of a patient that requires minimal calculation time.

A further object of the present invention is to provide an automatic calibration of the determined change in the thoracic cage volume.

Yet another object of the present invention is to provide a device for measuring the lung volume of an immobile patient.

These and other objects and advantages of the present invention will become readily apparent to those skilled in the art from a review of the following detailed description of the preferred embodiment in conjunction with the accompanying drawings in which like numerals in the several views refer to corresponding parts.

BRIEF DESCRIPTION OF THE DRAWINGS

FIG. 4 is a flow diagram of the process used to determine the lung volume of a patient.

DETAILED DESCRIPTION

Figure 1:
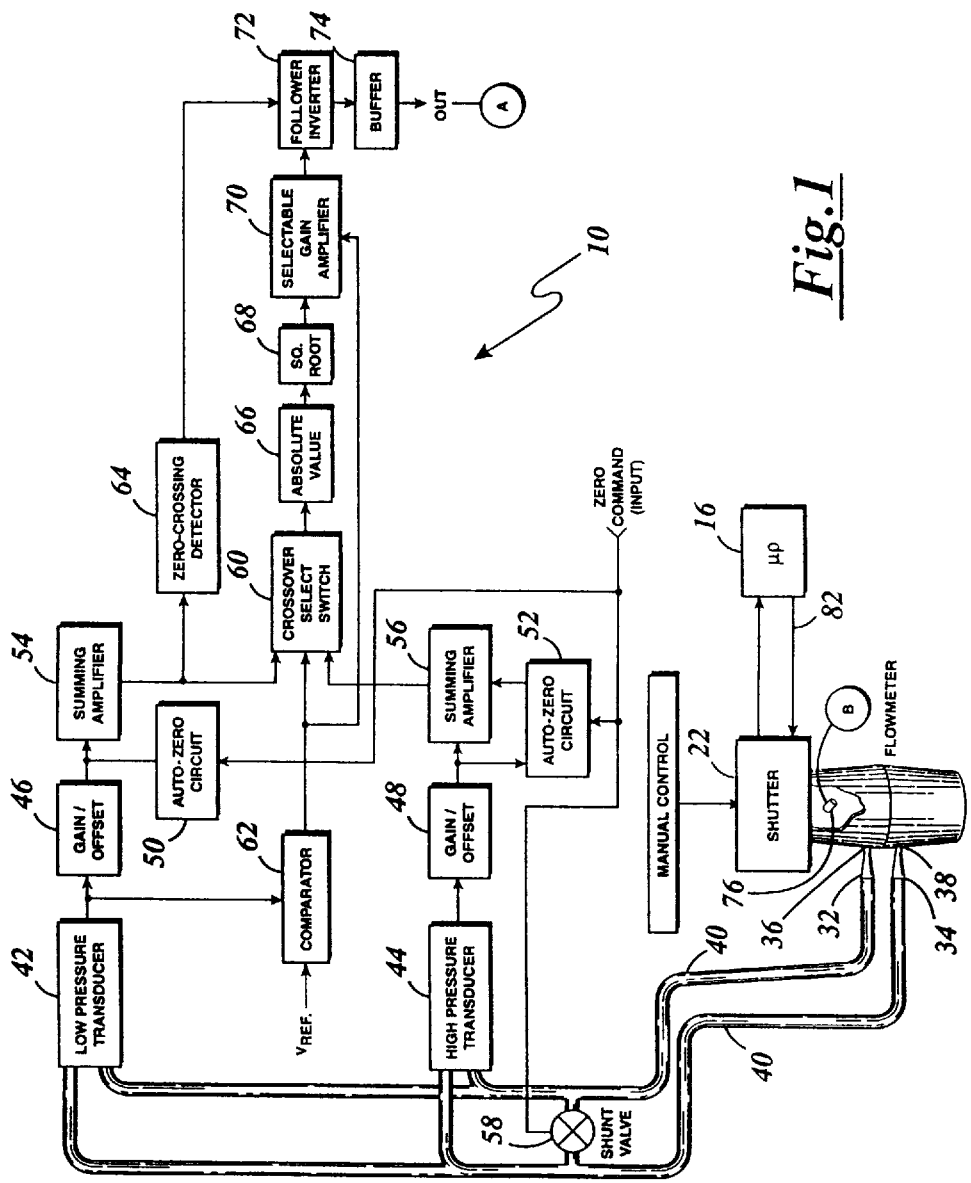
FIGS. 1 and 2 together are block diagrams of a preferred embodiment of the equipment employed in carrying out the invention.
Figure 2:
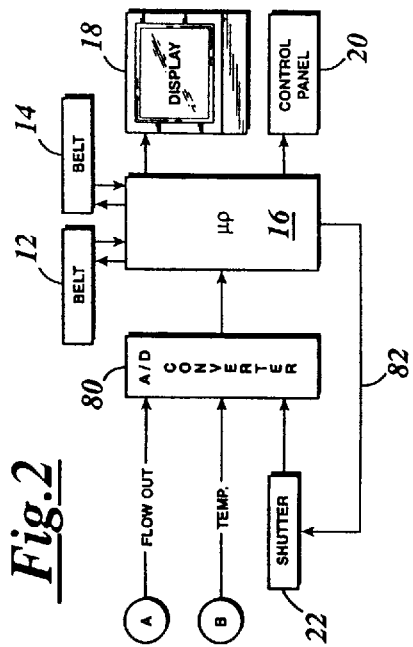

In conjunction with the figures, details of the representative embodiments will next be presented. Referring first to FIGS. 1 and 2, there is shown in block diagram form the equipment that may be employed in determining the lung volume of a patient. The lung volume measurement device of the present invention includes a flow meter 10, first and second body encircling impedance belts 12 and 14 respectively, a microprocessor-based controller 16, display 18, control panel 20, and shutter 22 coupled to the flow meter 10.

The flow meter 10 includes a mouthpiece 30 having needle probes 32 and 34 entering sampling ports 36 and 38. The needle probes 32 and 34 are coupled by appropriate tubular lines 40 to pressure transducers 42 and 44 in a low pressure channel and a high pressure channel respectively. The two transducers 42 and 44 are used to cover a pressure range of from 0.0001 to 40 inches water column. The low pressure transducer 42 has a full scale reading of about 0.5 inches water column while the high pressure transducer 44 may have a full scale of about 40 inches water column. The output of each of these transducers, after appropriate gain adjustment and offset compensation by circuits 46 and 48 comprises an analog signal with full scale output of each transducer corresponding to a positive or negative 10 volts, depending upon which side of the pressure transducer is at a higher pressure than the opposite side.

When there is a zero pressure differential, the output of each of the transducers should be at zero volts. Should small deviations from zero occur, they can be compensated for by means of an auto zero circuit 50 for the low pressure side and a corresponding circuit 52 for the high pressure side. The auto zero circuits are configured so that the signal input thereto is amplified and converted to a digital value proportional to pressure which is then stored in a buffer circuit. The contents of the buffer are then converted back into an analog signal form. The analog signal is inverted and attenuated to an appropriate level so that when it is summed with the original signal in a summing amplifier, as at 54 and 56, the result will be zero volts. The contents of the buffer in the auto zero circuits 50 and 52 are updated, on command, during a time interval when it is known that there is a zero pressure difference across the two needle probes 32 and 34. This condition is established by means of a shunt valve 58 which is opened by the same "zero" command.

The output of one or the other of the transducers 42 and 44 is passed along to the next stage through a switch 60 referred to as the "crossover select switch". Switch 60 is controlled by a signal produced by a comparator 62 which is configured to monitor the output of the low pressure transducer 42. When the output of that transducer is nearly full scale in either direction, the signal from the comparator 62 changes state, so that the output of the high pressure transducer 44 will be passed through the cross-over select switch 60 instead of the low pressure signal. It should also be noted that the output of the comparator 62 is used to select a gain value at a later amplifier stage.

The amplified, zero-corrected output of the low pressure transducer at the output of summing amplifier 54 is also connected to a zero-crossing detector 64 whose output is used to re-introduce the appropriate algebraic sign in the signal at a later stage. The signal selected by the cross-over switch 60 is applied to an analog circuit (absolute value) 66 that has a voltage output equal to the absolute value of the input voltage. This signal is passed to a square root circuit 68 whose voltage output is equal to the square root of the voltage applied to its input. The output of the square root circuit is amplified by a variable gain stage 70 whose value of the gain is controlled by the same signal that is used to control the state of the cross-over select switch 60. The gains are adjusted so that when the pressure is just sufficient to change the signal being acted upon by the absolute value and square root circuits 66 and 68, the output of this gain stage 70 will be piecewise continuous. The signal is then acted upon by follower inverter stage 72. The output of this stage is either equal to the input to the stage, or equal to the negative of the input to this stage, depending on the output of the zero-crossing detector 64.

Figure 3:
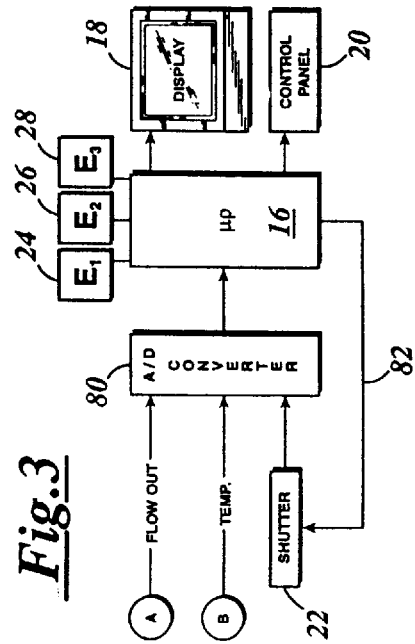
FIG. 3 is a block diagram of another embodiment of a portion of the equipment employed in carrying out the invention.

From the output of the follower inverter stage 72, the signal is buffered by a unity gain amplifier 74 before it is provided as the value of the flow measured in units of milliliters per second or liters per second, depending upon whether the low pressure transducer 42 or high pressure transducer's 44 output is being processed. The flow information output is applied to an A/D converter 80 and then fed to the microprocessor-based controller 16 (see connector A and FIGS. 2 or 3). A temperature transducer 82 and shutter 22 are sealably engaged to the mouthpiece 30 of the flow meter 10. Output from the temperature transducer 82 and shutter 22 are likewise fed through A/D converter 80 and then to the controller 16 for processing (see connector B and FIGS. 2 or 3). The microprocessor-based controller 16 controls the actuation of the shutter through line 82.

The controller 16 includes a power supply 30, microprocessor chip, ROM memory for storing a program of instructions to be executed by the microprocessor, and a RAM memory for storing operands and identifier values corresponding to the output signals of the impedance belts 12 and 14, the flow output, temperature transducer 76 and shutter 22. Those skilled in programming a typical microprocessor are in a position to write the detailed code to determine the lung volume of a patient from what is presented in the flow diagram of FIG. 3, the explanation that follows, and utilizing the output signals transmitted from the impedance belts 12 and 14, the flow output, temperature transducer 76 and shutter 22. A value associated with a measured barometric pressure may be input into the microprocessor based controller 16 through control panel 20 or a barometric pressure transducer may be electrically coupled to the controller 16.

The first and second impedance belts 12 and 14 are battery powered and are intended to separately monitor the chest and abdominal motions associated with the respiration of a patient. Associating the chest movement and lung volume change to respiration is accomplished by monitoring minute changes in the electrical impedance of a one turn coil of wire contained in each belt 12, 14 and surrounding the rib cage and abdominal areas of the patient. Of course, the length of the coil of wire may be altered according to the size of the patient. Each belt 12, 14 includes an impedance matching transformer and provides a separate signal output associated with the impedance of the coil which is electrically transmitted to an LC oscillator circuit coupled to the micro-controller 16.

The output signals for each belt 12 and 14 are band pass filtered and also have a re-zeroing function. The band pass filter is electrically coupled to the electronic circuit of the controller 16 and is intended to filter out signals associated with large amplitude, short time constant transients such as motion artifacts corresponding to patient movement. The output signal of each belt 12 and 14 ranges between about a high of +1.2 volts to a low of −20 millivolts. Those skilled in the art will recognize that increasing the sensitivity of the amplifiers employed will decrease the amount of respiratory motion needed to generate a signal sufficient to determine the volume change in lung volume. The filtered output signals are integrated and differentiated by known means for phase alignment and derivation of a value associated with the change in volume of the lungs.

At the same time the change in volume is determined from the impedance belts 12 and 14, the change in pressure within the lungs is also determined. The flow meter 10 is used to determine the pressure change during each respiratory cycle. The mouthpiece 30 of the flow meter 10 is provided with a shutter or valve 22 of known construction and may be electro mechanically opened and closed by the micro controller 16. Alternatively, a manual control 84 may be used to actuate the shutter 22.

Prior to determining the change in pressure within the lungs, the flow meter 10 is used to determine a change of pressure within the mouthpiece 30 when the shutter is first open and then closed during the respiratory cycle. The patient is allowed to breath normally through the mouthpiece with the shutter open. The flow measured at the mouth is integrated to provide an amount associated with volume change and this amount is compared to the thoracic cage volume changes to derive a calibration factor to be applied to the determination of the change in the thoracic cage volume. The determination of the calibration factor may likewise be derived immediately following the determination of the change in pressure within the mouthpiece. The calibration and determination of a correction factor of the present invention occurs at a time sufficiently close in time to the determination of the thoracic gas volume to thereby eliminate the need to maintain a separate calibration relationship as the patient's position changes and at a time sufficient to minimize drift and sensor changes. Those skilled in the art will appreciate that the self calibration of the combined flow meter and impedance monitor eliminates the need for a separate calibration of the measured impedance changes from changes in the thoracic cage.

Once the calibration factor is determined, the shutter 22 is then closed for a predetermined time. When the shutter is closed, the pressure within the mouthpiece corresponds to the pressure within the lungs and may be measured by one of the pressure transducers 42 or 44. During each respiratory cycle, the change in pressure may likewise be measured and recorded. An output corresponding to the pressure within the mouthpiece 30 is transmitted from the pressure transducer 42 or 44 to the controller 16. From the pressure transducer output, the change in pressure may be determined and stored by the controller 16.

Knowing the change in pressure, change in lung volume and barometric pressure during a respiratory cycle, the patient's lung volume may be determined. Assuming the temperature is held constant during the respiratory cycle, it is known that $PV=P'V'$, where P is the barometric pressure, V is the thoracic gas volume to be measured, P' is the pressure changes in alveolar pressure and V' is associated with changes in the thoracic gas volume. P' can also be represented as $P'=(P-\Delta P)$ and V' may be represented as V'=(V+ΔV) where ΔP is the change in pressure (measured in the mouthpiece 30) and ΔV is the change in volume (measured by the first and second impedance belts 12 and 14). Substituting in for P' and V', PV may be represented as PV=(P-ΔP)(V+ΔV). Cross multiplying, PV=PV+PΔV-ΔPV-ΔPΔV. In this equation the amounts associated with ΔPΔV are insubstantial and there ΔPΔV is canceled from the equation leaving PV=PV+PΔV-ΔPV Subtracting PV from both sides results in 0=PΔV-ΔPV. Adding ΔPV to both sides, the equation then becomes ΔPV=PΔV. Solving for V, the equation then is V=P(ΔV/ΔP). Hence, knowing the barometric pressure, the ΔP from the flow meter 10 in the mouthpiece 30 and the ΔV from the first and second impedance belts 12 and 14, the microprocessor 16 may calculate the patient's lung volume incorporating the predetermined calibration factor into the determination of the patient's lung volume V. Those skilled in the art will appreciate that the calibration factor may be a linear, polynomial or other mathematical correction that correlates a measured change in thoracic cage volume to a measured change in volume in the mouthpiece.

In an alternate embodiment shown in FIG. 2, the microprocessor-based controller 16 is shown electrically coupled to electrodes 24–28. An output signal from each electrode 24–28 is transmitted to the microprocessor-based controller 16, wherein the output signal is converted to a value associated with the change in volume of the lungs.

In use, the user first attaches the belts 12 and 14, electrodes 24–28, or other detectors of known construction to the patient's torso (see block 90). The detection means is then coupled to the microprocessor-based controller 16. The patient then breaths through the mouthpiece 30. During a predetermined respiratory cycle of the patient, the shutter 22 is closed. While the shutter is closed, the output signals from the 15 belts 12 and 14 and the flow meter 10 are transmitted to the controller 16 for processing and storage. From the belts 12 and 14 output signals, the controller 16 determines the change of lung volume during a respiratory cycle (see block 92). The change in pressure in the mouthpiece during the respiratory cycle is also determined by the controller 16 from the output signals of one of the pressure transducers 42 or 44 (see block 96). The controller 16 also stores the barometric pressure (see block 94). Without any limitation intended, the barometric pressure is measured near the patient, within a proximity sufficient to minimizes changes in barometric pressure. From the measured change in volume, change in pressure and barometric pressure, the controller 16 is programmed to determine the thoracic gas volume for the respiratory cycle being observed (see block 98) by substituting the determined values into the above derived algebraic equation V=ΔV(P/ΔP) and applying the derived correction factor. The controller may then be programmed to automatically adjust auxiliary equipment based on the determined lung volume (see block 100).

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A portable apparatus for measuring a lung volume of a patient, said apparatus comprising:

(a) detection means attached to a torso of the patient, for detecting a volume change in the lung volume of the patient during a respiratory cycle;

(b) a flow meter including a mouthpiece having pressure transducers coupled thereto for sensing volume and pressure change during the respiratory cycle; and (c) a microprocessor-based controller electrically coupled to said detection means and said flow meter, said controller including calibration means for calibrating the apparatus and means for analyzing signals transmitted from said detection means and said flow meter and for calculating the lung volume of the patient from the analyzed signals, wherein a calibration of the apparatus depends upon a correlation between change in thoracic cage volume and change in volume sensed by the flow meter.

2. The apparatus as recited in claim 1, wherein said detection means comprises a first torso belt for detecting minute changes in the electrical impedance within a conductor surrounding a rib cage of the patient, wherein a signal associated with impedance changes in the conductor are transmitted to the controller.

3. The apparatus as recited in claim 2, wherein said detection means further comprises a second torso belt for detecting minute changes in the electrical impedance of a second conductor which surrounds an abdomen of the patient, wherein a second signal associated with impedance changes in the second conductor are transmitted to the controller.

4. The apparatus as recited in claim 1, wherein said detection means comprises a plurality of electrodes coupled to said controller for determining volume changes in the lung volume.

5. The apparatus as recited in claim 1, wherein said mouthpiece further includes a shutter for controlling a flow of air into and out of the mouthpiece.

6. A portable apparatus for measuring a lung volume of a patient, said apparatus comprising:

(a) detection means attached to a torso of the patient, for detecting a volume change in the lung volume of the patient during a respiratory cycle;

(b) a flow meter including a mouthpiece having pressure transducers coupled thereto for sensing volume and pressure change during the respiratory cycle;

(c) a shutter sealably coupled to an end of the mouthpiece; and (d) a microprocessor-based controller electrically coupled to said detection means and said flow meter, said controller including calibration means for calibrating the apparatus and means for analyzing signals transmitted from said detection means and said flow meter and for calculating the lung volume of the patient from the analyzed signals, wherein a calibration of the apparatus depends upon a correlation between change in thoracic cage volume and change in volume sensed by the flow meter.

7. The apparatus as recited in claim 6, wherein said detection means comprises a first torso belt for detecting minute changes in the electrical impedance within a conductor surrounding a rib cage of the patient, wherein a signal associated with impedance changes in the conductor are transmitted to the controller.

8. The apparatus as recited in claim 7, wherein said detection means further comprises a second torso belt for detecting minute changes in the electrical impedance of a second conductor which surrounds an abdomen of the patient, wherein a second signal associated with impedance changes in the second conductor are transmitted to the controller.

9. The apparatus as recited in claim 6, wherein said detection means comprises a plurality of electrodes coupled to said controller for determining volume changes in the lung volume.

10. The apparatus as recited in claim 6, wherein said shutter is electrically coupled to said microprocessor based controller, wherein the microprocessor based controller transmits a signal to said shutter to thereby actuate the shutter between an open and closed position.

11. A method of measuring the thoracic gas volume of a patient's lungs utilizing a noninvasive apparatus, said method comprising the steps of:
   (a) attaching a detection means to a torso of the patient, wherein said detection means detects a change in the lung volume of the patient;
   (b) measuring a change of thoracic cage volume during a patient's respiratory cycle;
   (c) determining the barometric pressure in an area near the patient;
   (d) measuring a change of pressure in a mouthpiece as the patient breathes through the mouthpiece; and
   (e) determining the thoracic gas volume from the measured change of thoracic cage volume, change of pressure in the mouthpiece and measured barometric pressure.

12. The method as recited in claim 11, wherein measuring a change of thoracic cage volume further includes determining a change of impedance in a conductor of a torso belt attached to a torso of the patient as the patient inhales and exhales, and associating the change of impedance with the change of lung volume as measured in the mouthpiece by a means for measuring the change of volume within the mouthpiece.

13. The method as recited in claim 11, further comprising the steps of measuring a change in thoracic cage volume and a change in volume within the mouthpiece; deriving a correction factor that correlates the measured change in thoracic cage volume to the measured change in volume within the mouthpiece; and then applying the derived correction factor during the determination of the thoracic gas volume.

14. The method as recited in claim 13, wherein the noninvasive apparatus is calibrated immediately prior to the determination of the thoracic gas volume.

15. The method as recited in claim 13, further comprising the step of calibrating the noninvasive apparatus at a time sufficient to minimize drift and sensor changes of the apparatus.

16. The method as recited in claim 15, wherein the correction factor is determined after the determination of the thoracic gas volume and the correction factor is then applied to the determined thoracic gas volume.

17. The method as recited in claim 11, further comprising the step of adjusting auxiliary equipment based on the determined thoracic gas volume.

* * * * *